United States Patent [19]
Cen et al.

[11] Patent Number: 6,165,733
[45] Date of Patent: Dec. 26, 2000

[54] γ II ADAPTIN

[75] Inventors: Hui Cen, Oakland; Lewis T. Williams, Tiburon, both of Calif.

[73] Assignee: Chiron Corporation, Emeryville, Calif.

[21] Appl. No.: 08/861,745

[22] Filed: May 22, 1997

Related U.S. Application Data

[60] Provisional application No. 60/019,462, Jun. 13, 1996, and provisional application No. 60/018,162, May 23, 1996.

[51] Int. Cl.$^7$ .............................. C12Q 1/00; C12N 15/62; C07K 14/46
[52] U.S. Cl. ........................... 435/7.21; 435/4; 435/69.7; 435/325; 436/501; 536/23.5; 530/350
[58] Field of Search ............................. 435/7.21, 4, 69.7, 435/325; 436/501; 536/23.5; 530/350

[56] References Cited

U.S. PATENT DOCUMENTS 5,283,173  2/1994  Fields et al. ................................ 435/6

FOREIGN PATENT DOCUMENTS

93/21328  10/1993  WIPO .

OTHER PUBLICATIONS

Gaidarov et al. A functional phosphatidylinositol 3,4,5–trisphosphate/phosphoinositide binding domain in the clathrin adaptor AP–2 alpha subunit. Implications for the endocytic pathway. J Biol Chem, (Aug. 23, 1996) 271 (34) 20922–9.
Otsu et al. Characterization of two 85 kd proteins that associate with receptor tyrosine kinases, middle–T/pp60c–src complexes, and PI3–kinase. Cell, (Apr. 5, 1991) 65 (1) 91–104, May 1991.
Hiles et al. Phosphatidylinositol 3–kinase: structure and expression of the 110 kd catalytic subunit. Cell, (Aug. 7, 1992) 70 (3) 419–29.
Pearse, "Receptors Compete for Adaptors Found in Plasma Membrane Coated Pits" *EMBO Journal* 7(11):3331–3336, 1988.
Pearse and Robinson, "Clathrin, Adaptors, and Sorting" *Annu. Rev. Cell Biol.* 6:151–171, 1990.
Robinson, "Cloning and Expression of γ–Adaptin, a Component of Clathrin–Coated Vesicles Associated with the Golgi Apparatus" *J. Cell Biology* 111(No. 6, pt. 1):2319–2326, Dec., 1990.
Trowbridge, "Endocytosis and Signals for Internalization" *Current Opinion Cell Biology* 3:634–641, 1991.
Sorkin and Carpenter, "Interaction of Activated EGF Receptors with Coated Pit Adaptins" *Science* 261:612–615, Jul., 1993.
Cohen et al., "The Conserved C–Terminal Domain of the Bovine Papillomavirus E5 Oncoprotein can Associate with an α–Adaptin–Like Molecular: a Possible Link Between Growth Factor Receptors and Viral Transformation" *Molecular and Cellular Biology* 13(10):6462–6468, Oct., 1993.
Zhang et al., "Synaptotagmin I is a High Affinity Receptor for Clathrin AP–2: Implications for Membrane Recycling" *Cell* 78:751–760, Sep., 1994.
Ohno et al., "Interaction of Tyrosine–Based Sorting Signals with Clathrin–Associated Proteins" 269:1872–1875, Sep., 1995.
Okabayashi et al., "Interaction of Shc with Adaptor Protein Adaptins" *J. Biological Chemistry* 271(9):5265–5269, 1996.
Lewin et al., *Molecular Biology of the Cell* (Supplement) (1996) 7:279a.

*Primary Examiner*—Elizabeth Kemmerer
*Assistant Examiner*—David S. Romeo
*Attorney, Agent, or Firm*—Banner & Witcoff; Jane E. R. Potter; Robert P. Blackburn

[57] ABSTRACT

A mammalian protein involved in receptor-mediated endocytosis specifically binds to phosphatidylinositol 3-kinase. More specifically it binds to the *Bcr* homology domain of the p85 subunit of phosphatidylinositol 3-kinase. Phathoidylinositol 3-kinase also binds to platelet derived growth factor receptor. Other receptors may also bind, including those for insulin, insulin-like growth factor-1, colony stimulating factor 1, nerve growth factor, hepatocyte growth factor, stem cell growth factor, and epidermal growth factor. Mitogenesis is the consequence of the binding and internalization of these growth factors. Inhibition of the process of receptor-mediated internalization inhibits mitogenesis.

2 Claims, No Drawings

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 791 amino acids
      (B) TYPE: amino acid
      (C) STRANDEDNESS: single
      (D) TOPOLOGY: linear (ii) MOLECULE TYPE: None (xi) SEQUENCE DESCRIPTION: SEQ ID NO:1:

```
Met Val Val His Ser Leu Arg Leu Gln Asp Leu Ile Glu Glu Ile Arg
 1               5                  10                  15
Gly Ala Lys Thr Gln Ala Gln Glu Arg Glu Val Ile Gln Lys Glu Cys
                20                  25                  30
Ala Gln Ile Arg Ala Ser Phe Arg Asp Gly Asp Pro Leu Gln Arg His
            35                  40                  45
Arg Gln Leu Ala Lys Leu Leu Tyr Val His Met Leu Gly Tyr Pro Ala
        50                  55                  60
His Phe Gly Gln Met Glu Cys Leu Lys Leu Ile Ala Ser Pro Arg Phe
65                  70                  75                  80
Thr Asp Lys Arg Val Gly Tyr Leu Gly Ala Met Leu Leu Leu Asp Glu
                85                  90                  95
Arg His Asp Ser His Leu Leu Ile Thr Asn Ser Ile Lys Asn Asp Leu
            100                 105                 110
Ser Gln Gly Asn Gln Pro Val Gln Gly Leu Ala Leu Cys Thr Leu Ser
        115                 120                 125
Thr Met Gly Ser Ala Glu Met Cys Arg Asp Leu Ala Pro Glu Val Glu
130                 135                 140
Lys Leu Leu Leu Gln Pro Ser Pro Tyr Val Arg Lys Lys Ala Ile Leu
145                 150                 155                 160
Thr Ala Val His Met Ile Arg Lys Asp Pro Glu Leu Ser Gly Ile Phe
                165                 170                 175
Leu Pro Pro Cys Thr Lys Leu Leu Arg Glu Arg His His Gly Ile Gln
            180                 185                 190
Leu Gly Thr Val Thr Leu Ile Thr Glu Leu Cys Glu Arg Asn Pro Ala
        195                 200                 205
Ala Leu Arg His Phe Arg Lys Val Val Pro Gln Leu Val Gln Ile Leu
210                 215                 220
Arg Thr Leu Val Thr Thr Gly Tyr Ser Thr Glu His Ser Ile Ser Gly
225                 230                 235                 240
Val Ser Asp Pro Phe Leu Gln Val Gln Ile Leu Arg Leu Leu Arg Ile
                245                 250                 255
Leu Gly Arg Asn His Glu Glu Ser Glu Thr Met Asn Asp Leu Leu
            260                 265                 270
Ala Gln Val Ala Thr Asn Thr Asp Thr Ser Arg Asn Ala Gly Asn Ala
        275                 280                 285
Val Leu Leu Glu Thr Val Leu Thr Ile Met Ala Ile His Ser Ala Ala
290                 295                 300
Gly Leu Arg Val Leu Ala Val Asn Ile Leu Gly Arg Phe Leu Leu Asn
305                 310                 315                 320
```

-continued

```
Asn Asp Lys Asn Ile Arg Tyr Val Ala Leu Thr Ser Leu Leu Gln Leu
            325                 330                 335

Val Gln Ser Asp His Ser Ala Val Gln Arg His Arg Ser Thr Val Val
            340                 345                 350

Glu Cys Leu Gln Glu Thr Asp Ala Ser Leu Ser Arg Arg Ala Leu Glu
            355                 360                 365

Leu Ser Leu Ala Leu Val Asn Ser Ser Asn Val Arg Ala Met Met Gln
370                 375                 380

Glu Leu Gln Ala Phe Leu Glu Ser Cys Pro Pro Asp Leu Arg Ala Asp
385                 390                 395                 400

Cys Ala Ser Gly Ile Leu Leu Ala Ala Glu Arg Phe Ala Pro Ser Lys
            405                 410                 415

Arg Trp His Ile Asp Thr Ile Leu His Val Leu Thr Thr Ala Gly Ala
            420                 425                 430

His Val Arg Asp Asp Ala Val Ala Asn Leu Thr Gln Leu Ile Gly Glu
            435                 440                 445

Ala Glu Glu Leu His Thr Tyr Ser Val Arg Arg Leu Tyr Ser Ala Leu
450                 455                 460

Ala Glu Asp Ile Ser Gln Gln Pro Leu Val Gln Val Ala Ala Trp Cys
465                 470                 475                 480

Ile Gly Glu Tyr Gly Asp Leu Leu Glu Gly Asn Cys Glu Glu Thr
            485                 490                 495

Glu Pro Phe Gln Val Glu Glu Asp Val Leu Ala Leu Leu Glu Lys
            500                 505                 510

Val Leu Gln Ser His Met Ser Leu Pro Ala Thr Arg Gly Tyr Ala Ile
            515                 520                 525

Thr Ala Leu Met Lys Leu Ser Thr Arg Leu Arg Gly Asp Asn Asn Arg
            530                 535                 540

Ile Arg Gln Val Val Ser Ile Tyr Gly Ser Cys Val Asp Leu Glu Leu
545                 550                 555                 560

Gln Gln Arg Ala Val Glu Tyr Asn Thr Leu Phe Gln Lys Tyr Asp His
            565                 570                 575

Met Arg Ala Ala Ile Leu Glu Lys Met Pro Leu Val Glu Arg Gly Asp
            580                 585                 590

Pro His Val Lys Glu Gly Gly Lys Glu Lys Gln Thr Glu Ala Gln Pro
            595                 600                 605

Leu Glu Val Thr Ala Pro Ala Pro Thr Glu Pro Gln Ala Thr Lys Leu
610                 615                 620

Leu Asp Leu Leu Asp Leu Leu Gly Asp Thr Ser Glu Pro Leu Ser Ser
625                 630                 635                 640

Gly His Ala Gln His Leu Pro Pro Gln Thr Pro Ser Pro Gly Glu Ala
            645                 650                 655

Leu Ile His Leu Leu Asp Leu Pro Cys Thr Pro Pro Pro Ala Pro
            660                 665                 670

Ile Pro Ser Val Arg Val Phe Glu Arg Glu Gly Leu Gln Leu Asp Leu
            675                 680                 685

Ser Phe Met Arg Pro Leu Glu Thr Pro Ala Leu Leu Leu Val Thr Ala
            690                 695                 700

Thr Thr Thr Asn Ser Ser Lys Glu Asp Val Thr His Phe Val Cys Gln
705                 710                 715                 720

Ala Ala Val Pro Lys Ser Phe Gln Leu Gln Leu Gln Ala Pro Ser Gly
            725                 730                 735

Asn Thr Ile Pro Ala Gln Gly Gly Leu Pro Ile Thr Gln Val Phe Arg
            740                 745                 750
```

Ile Leu Asn Pro Asn Gln Ala Pro Leu Arg Leu Lys Leu Arg Leu Thr
          755                 760                 765

Tyr Asn His Ser Gly Gln Pro Val Gln Glu Ile Phe Glu Val Asp Asn
      770                 775                 780

Leu Pro Val Glu Thr Trp Gln
785                 790

(2) INFORMATION FOR SEQ ID NO:2:

(i) SEQUENCE CHARACTERISTICS:
        (A) LENGTH: 2533 base pairs
        (B) TYPE: nucleic acid
        (C) STRANDEDNESS: double
        (D) TOPOLOGY: linear (xi) SEQUENCE DESCRIPTION: SEQ ID NO:2:

```
TCGAGCTACG TCAGGGCCGA AGCCAGGATG GTGGTGCATT CGTTGAGACT TCAGGACCTA      60

ATCGAAGAGA TTCGCGGGGC CAAGACGCAG GCCCAGGAAC GGGAGGTGAT CCAGAAGGAG     120

TGCGCCCAAA TTCGGGCCTC CTTCCGCGAT GGGGATCCCC TGCAGAGGCA TCGCCAGCTG     180

GCCAAACTGC TCTACGTCCA CATGTTGGGC TACCCCGCCC ACTTTGGACA GATGGAGTGC     240

CTGAAACTGA TCGCCTCCCC CAGATTCACA GACAAGAGGG TGGGCTACCT TGGGGCCATG     300

CTTCTATTGG ATGAGAGGCA CGATTCCCAT CTGCTCATCA CCAACAGCAT CAAGAATGAC     360

CTGAGCCAAG GAACCAGCC AGTTCAAGGC CTGGCCCTGT GTACTCTGAG TACCATGGGC      420

TCTGCTGAGA TGTGCCGGGA CCTAGCCCCT GAGGTGGAAA AGCTGCTTCT GCAGCCCAGT     480

CCCTATGTGC GGAAGAAGGC TATTTTGACT GCAGTGCACA TGATCCGGAA GGACCCTGAG     540

CTCTCCGGCA TCTTCCTCCC ACCTTGTACC AAACTGCTTC GTGAGCGTCA TCATGGCATC     600

CAGCTGGGCA CAGTCACGCT GATCACGGAG CTCTGTGAAA GAAACCCTGC AGCCCTCAGG     660

CACTTTCGCA AGGTAGTGCC GCAGCTGGTA CAGATCCTCC GGACTCTGGT GACTACAGGA     720

TACTCCACGG AGCACAGCAT CTCTGGAGTC AGCGACCCCT TCTTGCAGGT CCAGATACTC     780

CGCCTACTTC GGATCCTGGG ACGGAACCAT GAAGAAAGTA GCGAGACCAT GAACGACTTG     840

CTGGCCCAGG TCGCCACCAA CACAGACACC AGCCGAAATG CAGGCAACGC TGTCCTGTTG     900

GAAACAGTGC TTACCATCAT GGCCATCCAC TCTGCTGCTG GCCTCCGGGT TCTAGCTGTT     960

AACATTCTTG GTCGTTTCTT GCTCAACAAT GACAAGAATA TTAGGTATGT GGCTCTGACA    1020

TCATTGCTGC AGCTGGTGCA GTCTGACCAC AGTGCTGTAC AACGTCACCG GTCCACTGTG    1080

GTGGAGTGTC TACAGGAAAC GGACGCCTCC CTTAGCAGGC GGGCCCTGGA GCTGAGCCTG    1140

GCTCTGGTGA ACAGCTCCAA TGTACGAGCC ATGATGCAGG AGCTGCAGGC CTTTCTGGAG    1200

TCCTGCCCCC CTGATCTTCG GGCTGATTGT GCCTCAGGCA TTCTGTTGGC TGCGGAGAGG    1260

TTTGCTCCCA GCAAGCGATG GCACATAGAC ACCATCCTGC ACGTGCTGAC CACGGCAGGA    1320

GCCCATGTGA GGGATGACGC AGTGGCCAAC CTGACCCAGC TGATTGGAGA GGCCGAGGAG    1380

CTGCATACCT ACTCTGTGCG CCGTCTCTAC AGTGCCTTAG CAGAGGATAT CTCCCAGCAA    1440

CCACTGGTTC AGGTGGCAGC CTGGTGCATT GGCGAGTATG GGACCTCCT GCTGGAAGGT    1500

AACTGTGAGG AGACGGAGCC TTTTCAGGTG GAAGAAGAGG ACGTGCTAGC ACTGCTGGAA    1560

AAGGTGCTGC AGTCCCATAT GTCCCTGCCA GCCACTCGGG CTACGCCAT CACAGCCCTC     1620

ATGAAGCTGA GCACCCGACT CCGGGGAGAC AACAATCGTA TTCGCCAGGT GGTGTCCATC    1680

TACGGGAGCT GTGTGGACTT AGAGCTGCAA CAGCGGGCTG TGGAGTATAA CACACTCTTC    1740

CAGAAGTACG ACCACATGAG AGCCGCCATC CTAGAAAAGA TGCCTCTTGT AGAGCGTGGT    1800
```

```
GACCCCCACG TTAAAGAGGG AGGGAAGGAG AAGCAAACGG AAGCCCAGCC CTTGGAAGTG    1860

ACAGCCCCTG CCCCCACAGA ACCCCAGGCC ACCAAACTCT TAGATCTACT GGATCTCCTG    1920

GGTGACACTT CAGAGCCTCT CTCTTCTGGG CATGCCCAGC ATCTTCCTCC TCAGACTCCT    1980

TCCCCAGGGG AAGCCTTAAT TCATCTCCTT GACCTTCCCT GTACACCGCC ACCCCCAGCT    2040

CCCATCCCCA GTGTCAGAGT GTTTGAGCGT GAGGGCCTAC AGCTGGATCT TTCTTTCATG    2100

CGGCCCTTGG AGACCCCTGC TTTGCTCTTA GTCACTGCCA CCACCACCAA CTCCTCAAAG    2160

GAGGATGTTA CCCACTTCGT TTGCCAGGCA GCTGTGCCCA AGAGTTTCCA GCTGCAGTTA    2220

CAGGCCCCCA GTGGGAACAC AATTCCAGCT CAGGGTGGTC TTCCCATCAC CCAGGTCTTC    2280

AGAATCCTCA ATCCTAACCA GGCACCTTTG CGACTTAAGC TGCGCCTCAC CTACAACCAC    2340

TCTGGCCAGC CAGTACAGGA GATCTTTGAG GTGGATAACT TGCCTGTGGA GACGTGGCAG    2400

TAACCGACTG TGGTCAGTGT CTGGCCTGGG TGTCTCCAGG CTCCTGGTGT TCAAGGAACG    2460

GAAATAAAGA CCCACGTAAA TGGCGAAGTA AACTTTATTT AAAGGCGACG TCAGGGCCCT    2520

GACGTAGCTC GAG                                                      2533
```

(2) INFORMATION FOR SEQ ID NO:3:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:3:

```
Val Glu Arg Gly Asp Pro His Val Lys Glu Gly Lys Glu Lys Gln
 1               5                  10                  15

Thr Glu Ala Gln Pro Gly Ser Gly Ser
            20                  25
```

(2) INFORMATION FOR SEQ ID NO:4:

(i) SEQUENCE CHARACTERISTICS:
        (A) LENGTH: 189 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:4:

```
Lys Leu Val Glu Ala Ile Glu Lys Lys Gly Leu Glu Cys Ser Thr Leu
 1               5                  10                  15

Tyr Pro Thr Gln Ser Ser Ser Asn Pro Ala Glu Leu Arg Gln Leu Leu
            20                  25                  30

Asp Cys Asp Thr Ala Ser Leu Asp Leu Glu Met Phe Asp Val His Val
        35                  40                  45

Leu Ala Asp Ala Phe Lys Arg Tyr Leu Leu Asp Leu Pro Asn Pro Val
    50                  55                  60

Ile Pro Val Ala Val Ser Ser Glu Leu Ile Ser Leu Ala Pro Glu Val
65                  70                  75                  80

Gln Ser Ser Glu Glu Tyr Ile Gln Leu Ile Lys Lys Leu Ile Arg Ser
                85                  90                  95

Pro Ser Leu Pro His Gln Tyr Trp Leu Thr Leu Gln Tyr Leu Leu Lys
            100                 105                 110
```

```
His Phe Phe Lys Leu Ser Gln Thr Ser Ser Lys Asn Leu Leu Asn Ala
        115                 120                 125

Arg Val Leu Ser Glu Leu Phe Ser Pro Leu Leu Phe Arg Phe Pro Ala
    130                 135                 140

Ala Ser Ser Glu Asn Thr Glu His Leu Ile Lys Ile Ile Glu Ile Leu
145                 150                 155                 160

Ile Ser Thr Glu Trp Asn Glu Arg Gln Pro Ala Pro Ala Leu Pro Pro
                165                 170                 175

Lys Pro Pro Lys Pro Thr Thr Val Ala Asn Asn Gly Met
                180                 185

(2) INFORMATION FOR SEQ ID NO:5:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:5:

Met Glu Gln Lys Leu Ile Ser Glu Glu Asp Leu
1               5                   10
```

γ II ADAPTIN

This application is a continuation-in-part of U.S. Ser. No. 60/019,462 filed Jun. 13, 1996, and U.S. Ser. No. 60/018,162 filed May 23, 1996, the disclosures of which are expressly incorporated herein.

BACKGROUND OF THE INVENTION

Receptor-mediated endocytosis is the mechanism by which a variety of nutrients, hormones, and growth factors are specifically and efficiently transported into the cell as described in Goldstein et al, *Annu. Rev. Cell Biol.* 1:1–39 (1985). During this process, receptors are selectively concentrated in clathrin-coated pits from which they are rapidly internalized and delivered to endosomes; some receptors like the low density lipoprotein (LDL) receptor are constitutively clustered and internalized in the absence of ligand, while others, such as the epidermal growth factor (EGF) receptor are concentrated in the coated pits and internalized only after binding ligand, as described in Trowbridge, *Current Opin. in Cell Biol.* 3:634–641 (1991). The protein complexes that link clathrin to transmembrane proteins are called adaptors. Plasma-membrane adaptors contain an α-adaptin and a β-adaptin subunit, while adaptors found in the Golgi apparatus contain a γ-adaptin and a β'-adaptin subunit, as described in Robinson, *J. of Cell Biol.* 111: 2319–2326 (1990).

Despite these general outlines of the process of receptor-mediated endocytosis, the identities of all of the molecules involved and the interactions among them are not known. Thus, there is a continuing need in the art for identification of components of this important process.

SUMMARY OF THE INVENTION

It is an object of the invention to provide a newly identified adaptin protein involved in receptor-mediated endocytosis.

It is an object of the invention to provide a fusion protein comprising a portion of the new adaptin molecule.

It is another object of the invention to provide an isolated polypeptide which consists of a portion of the new adaptin molecule.

It is still another object of the invention to provide a preparation of antibodies which specifically bind to the new adaptin molecule.

It is another object of the invention to provide a polynucleotide which encodes the new adaptin molecule.

It is yet another object of the invention to provide methods of screening for agents useful in inhibiting mitogenesis.

These and other objects of the invention are provided by one or more of the embodiments described below. In one embodiment of the invention an isolated and purified mammalian γ II-adaptin protein is provided. The protein binds to the *Bcr* homology domain of phosphatidylinositol 3-kinase.

In another embodiment of the invention a protein is provided which comprises the sequence shown in SEQ ID NO: 1.

In another embodiment of the invention a fusion protein is provided. The fusion protein comprises a first protein segment and a second protein segment fused to each other by means of a peptide bond, wherein the first protein segment consists of at least eight contiguous amino acids of a mammalian γ II-adaptin protein.

In yet another embodiment of the invention an isolated polypeptide is provided. The polypeptide consists of at least eight contiguous amino acids of a mammalian γ II-adaptin protein which binds to the *Bcr* homology domain of phosphatidylinositol 3-kinase.

In yet another embodiment of the invention an isolated preparation of antibodies is provided. The preparation specifically binds to a mammalian γ II-adaptin protein, wherein said protein binds to a *Bcr* homology domain as shown in amino acids 132–322 of SEQ ID NO: 4.

According to another embodiment of the invention a subgenomic polynucleotide is provided. The polynucleotide encodes a mammalian γ II-adaptin protein, wherein said protein binds to a *Bcr* homology domain of a p85 subunit of phosphatidylinositol 3-kinase.

According to still another embodiment of the invention a method of screening for agents useful in inhibiting mitogenesis is provided. The method comprises the steps of:

contacting a test compound with a mammalian γ II-adaptin and a protein comprising a *Bcr* homology domain, wherein the protein binds to the γ II-adaptin in the absence of the test compound;

determining the amount of at least one of γ II-adaptin and the protein which is bound or unbound in the presence of the test compound, wherein a test compound which decreases the amount bound or increases the amount unbound, of at least one of γ II-adaptin and the protein is an agent useful for inhibiting mitogenesis.

According to still another aspect of the invention, a method of screening test compounds to identify agents useful for inhibiting mitogenesis is provided. The method comprises the steps of:

contacting a cell with a test compound, wherein the cell comprises:

a first fusion protein comprising (1) a DNA binding domain and (2) all or a portion of a mammalian γ II-adaptin, wherein the portion is capable of binding to p85 subunit of phosphatidylinositol 3-kinase;

a second fusion protein comprising (1) a transcriptional activating domain and (2) all or a portion of a p85 subunit of phosphatidylinositol 3-kinase, said portion comprising a *Bcr* homology domain of p85 subunit of phosphatidylinositol 3-kinase consisting of amino acids 134–322 as shown in SEQ ID NO: 4, wherein the interaction of the first and second fusion proteins reconstitutes a sequence-specific transcriptional activating factor; and a reporter gene comprising a DNA sequence to which the DNA binding domain of the first fusion protein specifically binds; and measuring the expression of the reporter gene, wherein a test compound that decreases the expression of the reporter gene is a potential inhibitor of mitogenesis.

According to still another aspect of the invention another method is provided for screening test compounds to identify agents useful for inhibiting mitogenesis. The method comprises the steps of:

contacting a cell with a test compound, wherein the cell comprises:

a first fusion protein comprising (1) a DNA binding domain and (2) all or a portion of a p85 subunit of phosphatidylinositol 3-kinase, said portion comprising a *Bcr* homology domain of p85 subunit of phosphatidylinositol 3-kinase consisting of amino acids 134–322 as shown in SEQ ID NO: 4;

a second fusion protein comprising (1) a transcriptional activating domain and (2) all or a portion of a mammalian γ II-adaptin, wherein the portion is capable of binding to p85 subunit of phosphatidylinositol 3-kinase; wherein the interaction of the first and second fusion proteins reconstitutes a sequence-specific transcriptional activating factor; and a reporter gene comprising a DNA sequence to which the DNA binding domain of the first fusion protein specifically binds; and measuring the expression of the reporter gene, wherein a test compound that decreases the expression of the reporter gene is a potential inhibitor of mitogenesis.

The present invention thus provides the art with methods and reagents for drug discovery.

BRIEF DESCRIPTION OF THE SEQUENCES

SEQ ID NO: 1 provides the amino acid sequence of mouse γ II adaptin.

SEQ ID NO: 2 provides the polynucleotide sequence encoding mouse γ II adaptin.

SEQ ID NO: 3 provides a peptide sequence used for immunization of sheep.

SEQ ID NO: 4 provides the *Bcr* homology domain of phosphatidylinositol 3-kinase.

DETAILED DESCRIPTION OF THE PREFERRED EMBODIMENTS

The inventors have discovered a new member of the family of mammalian adaptin polypeptides. This polypeptide has been named γ II adaptin. The polypeptide binds to the *Bcr* homology domain of phosphatidylinositol 3-kinase (PI 3-kinase), shown in SEQ ID NO: 4. PI 3-kinase is described in Carpenter et al, *Mol. Cell. Biol.* 13: 1657–1665 (1993). While not wishing to be bound by any theory or mechanism of action proposed, it is believed that γ II adaptin, like other members of the adaptin family, is involved in receptor-mediated endocytosis.

Phosphatidylinositol 3-kinase binds to the receptor for PDGF. Upon PDGF (platelet derived growth factor) stimulation, cells are induced to undergo mitosis. In addition, the cellular localization of γ II adaptin has been found to change upon PGDF stimulation. Upon stimulation of resting cells with PGDF, the amount of γ II adaptin at the membrane is decreased, and the concentration of γ II adaptin in the perinuclear region increases. This change in localization is consistent with a role in endocytosis.

Mammalian γ II adaptin protein as provided herein can be isolated and purified according to conventional techniques. Provided with the sequence of the protein, antibodies can be routinely generated against all or portions of it. Antibodies can be affinity purified, using the γ II adaptin protein or polypeptide portions thereof. Such antibodies can, in turn, be used to purify γ II adaptin from cell lysates, for example, or to quantitate the amount of γ II adaptin in cells. Techniques for immunizing host animals to raise antiserum are well known in the art. Similarly, techniques for using such immunized host animals to raise monoclonal antibodies are also well known. Both types of antibodies are contemplated within the scope of the invention.

Mammalian γ II adaptin proteins and polypeptides can also be made using recombinant host cells. The nucleotide sequence of one gene which encodes a mammalian γ II adaptin protein is provided in SEQ ID NO: 2. This gene, or other genes which are obtained from other mammals by hybridization under stringent conditions, or modifications of the gene which retain the coding capacity for a protein which binds to the *Bcr* homology domain of phosphatidylinositol 3-kinase, can all be used in recombinant cells to produce a γ II adaptin protein. Preferably such pins will be at least 85%, and more preferably at least 90% identical to the sequence provided in SEQ ID NO: 1. Techniques for producing recombinant proteins given the nucleotide sequence encoding the protein are well known in the art. Selection of an appropriate technique is well within the purview of the skilled artisan. Portions of the gene can also be used to express portions of the γ II adaptin protein. These may be used, even if they do not retain the ability to bind to phosphatidylinositol 3-kinase, to raise antibodies, as discussed above. Typically a minimum number of contiguous amino acids to encode an epitope is 6, 8, or 10. However, more may be used, for example, at least 15, 25, 25, or 50, especially to form epitopes which involve non-contiguous residues.

Fusion proteins are also provided here, which comprise all or a portion of γ II adaptin covalently linked to a second protein or protein domain. Typically, at least 8 contiguous amino acids of γ II adaptin will be used, in order to constitute an epitope. The second protein can be an unrelated protein such as β-galactosidase or glutathione-S-transferase, which are useful for processing and purification with standard reagents. Alternatively, the second protein can harbor a transcription activation domain or a specific DNA binding domain. Such fusion proteins are useful for methods employing the two-hybrid technique, for example, in yeast cells. Techniques for making fusion proteins, either genetically or by covalently linking two proteins, are well known in the art. For some uses, such as in the two hybrid assays, it is desirable that the fusion protein retain the ability to bind to phosphatidylinositol 3-kinase.

Polynucleotide molecules which encode γ II adaptin are also provide herein. Such molecules are typically subgenomic, i.e., they are fragmented with respect to the state in which they exist in the genome. Thus they may comprise P1 or YAC genomic clones. They may also be cDNA clones, and thus intron-free. They may contain their own native expression control sequences, or they may be fused to expression control sequence from other genes or even other organisms, depending on the expression system in which they will be used. The polynucleotide molecules may be propagated in vectors, either prokaryotic or eukaryotic, and these may be maintained and expressed in host cells. Suitable vectors and host cells are available for many different purposes, and the particular choices are well within the skill of those in the art.

The polynucleotide molecules of the invention may encode portions of a γ II adaptin protein, especially those portions which retain binding ability to the p85 subunit of phosphatidylinositol 3-kinase. In addition, they may encode fusion proteins and polypeptide portions of γ II adaptin which are useful for raising antibodies. Typically these molecules will encode at least about 8 contiguous amino acids of γ II adaptin, and thus will comprise at least 24 contiguous γ II adaptin-encoding nucleotides. Such polynucleotides which encode less than a full length γ II adaptin are also useful as nucleotide probes for obtaining γ II adaptin variants and γ II adaptin genes from other species. Techniques for hybridizing polynucleotide probes and primers to obtain related family member genes are well known in the art.

Methods are provided for performing screening assays on agents which may be useful in inhibiting mitogenesis. The basis for all of these assays is the discovery of the binding interaction between γ II adaptin and phosphatidylinositol 3-kinase, and the functional consequence of the binding in mediation of the intracellular signaling of PGDF. Since PGDF is a known mitogen, agents which are found to inhibit the interaction of γ II adaptin and phosphatidylinositol 3-kinase will be useful in inhibiting mitogenesis.

According to one method a γ II adaptin and a protein comprising a Bcr homology domain are incubated together in the presence of a test compound. In the absence of the test compound the protein binds to γ II adaptin. The amount of bound and/or unbound proteins is determined according to any technique known in the art, including any immunological technique. In order to facilitate the assay, one of the proteins may be bound to a solid support, or may be labeled with a radiolabel, or other detectable label. A useful agent is identified which decreases the amount of protein bound or increases the amount of protein unbound. The proteins can be prebound prior to the introduction of the test compound, or the test compound can be contacted with one of the two binding partners prior to incubation. The protein which has a Bcr homology domain may be, for example, phosphatidylinositol 3-kinase, rho-GAP, n-chimerin, p190, Bem2, Bem3, 3BP1, Bcr, or phosphatidylinositol 3-kinase. Alternatively, a protein containing the Bcr homology domain of one of the proteins can be used.

A two-hybrid assay can also be used to assay for useful agents for inhibiting the interaction between γ II adaptin and phosphatidylinositol 3-kinase. According to such an assay, fusion proteins of each of the binding partners are used which each contain at least the domains necessary for the binding interaction. One of the binding partners is fused to a DNA binding domain and the other is fused to a transcriptional activating domain. The two fusion proteins interact to reconstitute a sequence-specific transcriptional activating factor. The two fusion proteins are produced in a cell which also contains a reporter gene which is sensitive to the activation of the reconstituted sequence-specific transcriptional activating factor. In the absence of test compound the cell expresses the reporter gene. Test compounds are added to the cell and the effect on the reporter gene's expression is monitored. A test compound which disrupts the binding of the γ II adaptin and the phosphatidylinositol 3-kinase domains will have a negative effect on the transcriptional activation ability of the reconstituted sequence-specific transcriptional activating factor. Thus the expression of the reporter gene will be reduced. The assay may also be conducted in the presence of agents which may bind directly or indirectly to phosphatidylinositol 3-kinase, including PGDF, insulin, IGF-1, CSF1, NGF, hepatocyte growth factor (HGF), stem cell growth factor, EGF.

EXAMPLE 1

Cloning the γ II Adaptin gene by Yeast 2-Hybrid System using Bcr homology domain of P85 as Bait The yeast 2-hybrid system as described in U.S. Pat. No. 5,283,173 and Chien et al, Proc. Nat'l Acad Sci USA 88:9578–9582 (1991) was used to screen a mouse thymus cDNA library, using the Bcr homology domain of the p85 subunit of PI 3 kinase as bait. See Cell 65:91–104 (1991), which teaches the characterization of two 85 kd proteins that associate with receptor tyrosine kinases, middle-T/pp66$^{c-src}$ complexes, and phosphatidylinositol 3-kinase.

Yeast stain Y190 is a Y153 derivative that is resistant to cyclohexamide (2.5 ug/ ml) due to a mutation in the CYH2 gene (genotype MATa gal4 gal80 his3 trp-1-901 ade2-101 ura3-52 leu2-3,-112+URA3::GAL→lacZ, LYS2::GAL (UAS)→HIS3 cyh$^1$). Y190 was supplied with 2-hybrid kits by Dr. Stephen J. Elledge of Baylor College of Medicine at Houston, Tex. A bait plasmid and a cDNA library cloned into vector PACT were transformed into strain Y190. The bait plasmid consisted of the Bcr homology domain of the p85 subunit of PI 3 kinase cloned into pASlCYH, a GAL4 DNA-binding domain fusion vector. Genes and Development 7.555–569. The prey plasmid PACT encodes the GAL 4 transactivation domain. Upon reconstitution of the GAl4 transcription activating factor, lacz and 1lS3 are induced. Transformants were selected for tryptophan prototrophy. Expression of the fusion protein was verified by western blotting with antibodies against the Bcr homology domain of the p85 subunit of PI 3 kinase. The resulting strain was confirmed by checking for its growth properties on SC-His plates containing 3-AT (3-aminotriazole, A8056, SIGMA, St. Louis, Mo.) and for its ability to activate the LacZ reporter. These tests were carried out relative to control strains carrying SNF1 in the pAS1 vector. 3-AT concentrations of 25 mM to 50 mM are sufficient to select against pAS1 clones that fail to activate transcription on their own. A strain that failed to activate transcription was selected for transformation by the mouse thymus cDNA library.

A colony was used to inoculate 50 ml of SC-Trp and grown overnight at 30° C. An optical density reading (OD) of the culture at absorbance of 600 nM was taken and the culture was subsequently diluted to 0.1 ($OD_{600}$) in 250 ml medium YEPD. [YEPD medium is made (for a one liter batch) with 10 g bacto-yeast extract, 20 g bacto-peptone, 20 g glucose, and 40 mg adenine sulfate.] Synthetic complete minus Trp media is used to select for pAS1 but YEPD gave the best transformation efficiencies.

The cells were harvested at 5,000 rpm for 7 to 8 minutes in a small laptop centrifuge. The cells were washed once with TE (approximately 20 mls) and resuspended in 20 mls LiSORB and incubated at 30° C. for 15 to 30 minutes. The cells were spun down as above and resuspended in 2 ml of LISORB (LiSORB consists of 100 mM LiOAc, 10 mM Tris pH 8, 1 mM EDTA, and 1M Sorbitol), and an aliquot of 100 ul was placed into each of 20 tubes, and held on ice.

The DNA carrier mix was then prepared by boiling 200 ul of 20 mg/ml sheared salmon sperm DNA for 7 to 10 minutes. 800 ul LiSORB at room temperature was added and mixed by pipetting up and down. The mixture was cooled to room temperature, making sure, however, that the temperature did not go below room temperature so that the mixture did not gel. Forty ug of mouse thymus library cDNA was added.

One hundred ul of the DNA mix was mixed with 100 ul of yeast Y190 cells in one of the 20 tubes of aliquoted cells. One hundred ul of the cells with DNA, 900 ul of 40% PEG-3350 in 100 mM LiAc/TE was added then the mixture was incubated at 30° C. for 30 minutes and the mixture was heat shocked at 42° C. for 5 minutes.

The cells were harvested and resuspended in 300 ul mls TE and plated at about 300 ul per 150 mm plate at 50 mM 3-AT. 30 ul of Sc-Trp Leu was plated to test transformation efficiency. Colonies that grow after 3 to 5 days were tested for β-galactosidase activity using a standard X-Gal colony filter assay. Blue colonies were taken for further study. The efficiency of transformation was about $5 \times 10^4$ to $10^5$ colonies per ug of cDNA library.

A positive control was pSE1111 (an SNF4 yeast transcription factor fused to the activation domain in pSE1107) and pSE1112 (an SNF1 yeast transcription factor fused to the DNA-binding domain of GALA in pAS1). These are both inserted as BamHI fragments and can serve as a positive control for X-gal staining and 3-AT resistance. A negative control was psF1112. The weak activation of pAS1 appears to decrease when genes are cloned into it.

Plasmids were harvested from the confirmed positive yeast colonies, which were then transformed into bacteria. Ten to 20 colonies of bacteria containing a library plasmid which is derived from a yeast colony were analyzed for the presence of library plasmid. The library plasmids were then reintroduced into yeast Y190 with the original bait (pAS-Bcr) or a PAS-lamin construct, to confirm the specificity of the interaction. One plasmid which encodes the 3' portion of γ II adaptin (amino acids 518–791) was found to specifically interact with the Bcr homology domain of p85.

A third test method for confirming positive clones was employed and involved switching the bait and prey in their respective plasmids because the majority of false positives will not interact in this test. Some true positives may not activate either in this switch, so only a positive result is reliable. The pAS1 polylinker has been placed into pACT to facilitate this transfer, creating pACT2.

All general yeast protocols in this example are described in Methods in Enzymology Vol. 194 "Guide to Yeast Genetics and Molecular Biology" by Guthrie and Fink. Also Ausubel et al (1994) CURRENT PROTOCOLS IN MOLECULAR BIOLOGY, (Greene Publishing Associates and John Wiley & Sons, New York, N.Y.), and Sambrook et al. (1989), MOLECULAR CLONING: A LABORATORY MANUAL, 2nd ed. (Cold Spring Harbor Press, Cold Spring Harbor, New York), are appropriate general references.

EXAMPLE 2
Generation of Polyclonal Antibodies In Sheep Against a Hydrophilic Peptide of γ II Adaptin Protein A 5.1 mg purified hydrophilic peptide of γ II adaptin protein was coupled through the terminal cysteine to diphtheria toxoid (DT) with the heterobifunctional cross-linking agent 6-maleimido-caproic acid N-hydroxysuccinimide ester (MCS) in the ration of 5.1 parts of peptide to 24.2 parts of DT (w/w).

The host selected for the immunization was a sheep Leicester/Merino cross, 3 to 5 years old. The immunization was conducted with a peptide-DT conjugate that was suspended in purified water at a concentration of 34.8 mg/ml, and emulsified by mixing with two volumes of Complete Freund's Adjuvant and injected intramuscularly, for a total volume of 1.0 ml (3.48 mg of conjugate, and 0.6 mg of peptide) per immunization. A second similar immunization followed 2 weeks later, this time using Incomplete Freund's Adjuvant. A third immunization, a boost, was performed on week 12 using Incomplete Freund's Adjuvant.

The animals were bled from the jugular vein using a cannula. The blood was heated at 37° C. for 30 minutes, chilled at 4° C. for 15 hours and centrifuged. The serum was stored at −20° C. On day 1 a pre-immune bleed was conducted, followed by the initial immunization. On day 14 the second immunization was conducted. On day 35 the first bleed was performed; on day 98 the second bleed; and on day 112 the third bleed.

All of the sera were tested with an enzyme linked immunosorbent assay (ELISA) with the carrier protein (DT) as coat. For all sera, the anti-peptide antibody titer was determined with an ELISA with a saturated level of the biotinylated form of the peptide (Ac-VERGDPHVKEGGKEKQTEAQP-GSGS-Biocytin-OH) (SEQ ID NO: 3) immobilized on an avidin coated microliter plate (500 ng/well). Also as a negative control, all sera were titrated on avidin only coated microtiter plates (without peptide coating). The assay was conducted by a standard biotin ELISA protocol. Either streptavidin or avidin can be used to coat the microtiter plates for the purpose of detecting anti-peptide antibodies because they produce similar activities.

The results were expressed as the reciprocal of the serum dilution that results in an absorbance of 1.0 above the background at 405 nm wavelength setting, and the background was established wit HRP-anti Sheep IgG conjugate and peroxidase dye. Two sheep were used to produce the polyclonal antibodies, sheep #2238 and #2239 and the results of the experiment indicated high antibody titer in crude sera with activity against DT, as compared to the controls as shown below.

| Sheep | prebleed | 2nd bleed | 4th bleed |
|---|---|---|---|
| activity against peptide | | | |
| 2238 | 5 ml/112 titer | 190 ml/882 titer | 340 ml/1567 titer |
| 2239 | 5 ml/68 titer | 290 ml/459 titer | 320 ml/1202 titer |
| activity against DT | | | |
| 2238 | 5 ml/128 titer | 190 ml/3232 titer | 340 ml/16416 titer |
| 2239 | 5 ml/ND titer | 290 ml/5888 titer | 320 ml/22976 titer |
| activity against Avidin | | | |
| 2238 | 5 ml/99 titer | 190 ml/98 titer | 340 ml/280 titer |
| 2239 | 5 ml/86 titer | 290 ml/50 titer | 320 ml/70 titer |

EXAMPLE 3
Co-Immunoprecipitation of γ II Adaptin with P85 Subunit Indicates the Function of γ II Adaptin The C-terminal one third of γ II adaptin cDNA encodes an ear portion of γ II adaptin molecule (amino acids 518–791), which is thought to interact with phosphatidylinositol 3-kinase, as does full-length γ II adaptin. Therefore, myc-tagged ear γ II was transfected into Cos cells. Cos cells transfected with myc-tagged ear portion of γ II adaptin were cultured and lysed. The myc tag is MEQKLISEEDL. (SEQ ID NO: 5) The cell lysate was immunoprecipitated with anti-p85 subunit of PI 3 kinase antibody. The precipitate was run on a reducing SDS-PAGE protein gel and transferred to a filter as described in Ausubel et al (1994) CURRENT PROTOCOLS IN MOLECULAR BIOLOGY, (Greene Publishing Associates and John Wiley & Sons, New York, N.Y.), and Sambrook et al. (1989), MOLECULAR CLONING: A LABORATORY MANUAL, 2nd ed. (Cold Spring Harbor Press, Cold Spring Harbor, New York), for a Western hybridization. The filter was then blotted first with anti-myc monoclonal antibody to detect myc-taggged γ II adaptin and then blotted with alkaline phosphatase-conjugated anti-mouse antibodies, and then the filter was developed with an NBT and BCIP omega, Madison, Wis.) system. The detection of a myc-tagged ear portion of γ II adaptin confirmed the interaction between p85 and γ II adaptin in the cells.

The reverse experiment using anti-myc antibody for immunoprecipitation and p85 for western blot also showed the co-immunoprecipitation between ear γ II and p85. Moreover, ear γ II was not found to complex with a p85 derivative that lacks the Bcr homology domain.

EXAMPLE 4
γ II adaptin-GFP Fusion Protein Is Internalized Upon PDGF Stimulation

A recombinant γ II adaptin-green fluorescent protein (GFP) fusion protein was constructed to investigate the distribution of γ II adaptin in the cell. The fusion protein was transfected into Cos cells. Transfected Cos cells were starved overnight with 0.5 % calf serum in DMEM. Both membrane and cytoplasmic distribution of γ II-GFP (green fluorescent protein) was observed in the starved cells. Upon 15 minutes PDGF (2 nM) stimulation at 37° C., many γ II-GFP transfected cells displayed partial perinuclear distribution, while the membrane and cytoplasmic distribution was greatly diminished.

We claim:

1. A method for screening test compounds to identify agents useful for inhibiting mitogenesis, comprising the steps of:
   (a) contacting a cell with a test compound, wherein the cell comprises:
      i) a first fusion protein comprising (1) a DNA binding domain and (2) all or a portion of a mammalian γ II adaptin having the amino acid sequence shown in SEQ ID NO: 1, wherein the portion binds to a p85 subunit of phosphatidylinositol 3-kinase;
      ii) a second fusion protein comprising (1) a transcriptional activating domain and (2) all or a portion of a p85 subunit of phosphatidylinositol 3-kinase, said portion comprising a Bcr homology domain of the p85 subunit of phosphatidylinositol 3-kinase consisting of amino acids 134–322 as shown in SEQ ID NO:4, wherein the interaction of the first and second fusion proteins reconstitutes a sequence-specific transcriptional activating factor; and
      iii) a reporter gene comprising a DNA sequence to which the DNA binding domain of the first fusion protein specifically binds; and
   (b) measuring the expression of the reporter gene, wherein a test compound that decreases the expression of the reporter gene is a potential inhibitor of mitogenesis.

2. A method for screening test compounds to identify agents useful for inhibiting mitogenesis, comprising the steps of:
   (a) contacting a cell with a test compound, wherein the cell comprises:
      i) a first fusion protein comprising (1) a DNA binding domain and (2) all or a portion of a p85 subunit of phosphatidylinositol 3-kinase, said portion comprising a Bcr homology domain of the p85 subunit of phosphatidylinositol 3-kinase consisting of amino acids 134–322 as shown in SEQ ID NO:4;
      ii) a second fusion protein comprising (1) a transcriptional activating domain and (2) all or a portion of a mammalian γ II adaptin having the amino acid sequence shown in SEQ ID NO: 1, wherein the portion binds to the p85 subunit of phosphatidylinositol 3-kinase; wherein the interaction of the first and second fusion proteins reconstitutes a sequence-specific transcriptional activating factor; and
      iii) a reporter gene comprising a DNA sequence to which the DNA binding domain of the first fusion protein specifically binds; and
   (b) measuring the expression of the reporter gene, a test compound that decreases the expression of the reporter gene being a potential inhibitor of mitogenesis.

* * * * *